(12) United States Patent
Jarnagin et al.

(10) Patent No.: US 6,238,874 B1
(45) Date of Patent: May 29, 2001

(54) CELL MOTILITY ASSAY

(75) Inventors: Kurt R. Jarnagin, San Mateo; Steven T. Kunitake, San Carlos; Bala S. Manian, Los Altos Hills, all of CA (US)

(73) Assignee: Biometric Imaging, Inc., Mountain View, CA (US)

( * ) Notice: Subject to any disclaimer, the term of this patent is extended or adjusted under 35 U.S.C. 154(b) by 0 days.

(21) Appl. No.: 09/363,247

(22) Filed: Jul. 28, 1999

Related U.S. Application Data

(60) Provisional application No. 60/094,401, filed on Jul. 28, 1998.

(51) Int. Cl.[7] .................................................. G01N 33/533
(52) U.S. Cl. ............... 435/7.21; 435/7.23; 435/7.24; 435/7.3; 435/29; 436/63; 436/514; 436/64; 436/172; 436/809
(58) Field of Search ........................... 435/29, 7.21, 7.23, 435/7.24, 7.3; 436/63, 514, 64, 172, 809

(56) References Cited

U.S. PATENT DOCUMENTS

| | | | |
|---|---|---|---|
| 4,412,246 | 10/1983 | Allen et al. ........................ | 358/107 |
| 5,302,515 | * 4/1994 | Goodwin, Jr. . | |
| 5,514,555 | * 5/1996 | Springer et al. . | |
| 5,601,997 | * 2/1997 | Tchao . | |
| 5,744,366 | 4/1998 | Kricka et al. ........................ | 436/63 |

OTHER PUBLICATIONS

Lee et al., Cytometry 21:120–128, 1995.*

* cited by examiner

Primary Examiner—Christopher L. Chin
Assistant Examiner—Bao-Thuy L. Nguyen
(74) Attorney, Agent, or Firm—Thomas Schneck; David M. Schneck

(57) ABSTRACT

An apparatus and method of use for assaying cellular motility in response to a concentration gradient of a chemotactic agent. Generally, the apparatus includes a chamber having a region for receiving a biological sample containing cells of interest and, spaced apart from such region, another region for receiving a chemotactic agent. Between these regions, a concentration gradient of chemotactic agent is established. The apparatus further includes an optical system for detecting and mapping the positions of individual cells responsive to such concentration gradient. Means for processing and analyzing the collected data are also provided. Motility determinations may be made on purified or unpurified samples. Single-site assay devices and multi-site, high-throughput assay devices are disclosed.

4 Claims, 7 Drawing Sheets

Time=0

FIG._3B

Time=0.5

FIG._3C

Time=1

FIG._3D

Time=1.5

FIG._3E

Time=2.0

CELL MOTILITY ASSAY

CROSS-REFERENCE TO RELATED APPLICATION

This application is related to U.S. provisional application S. No. 60/094,401 filed Jul. 28, 1998.

FIELD OF THE INVENTION

The present invention relates to an assay for determining the motility of cells. In particular, the invention provides an apparatus, and method of use, for determining the motile response of a selected type of cell to a given chemotactic agent.

BACKGROUND OF THE INVENTION

Chemotaxis is broadly defined as the orientation or movement of a cell or organism in relation to a chemical factor (Harris, 1954; Armstrong, 1985). Certain cells are capable of sensing a particular chemical factor and, in response, migrating toward or away from higher concentrations of the substance. In recent years, researchers and clinicians have expended great effort in studying cell motility for a number of cell types. Oftentimes, for example, it is useful for a clinician to determine the motility (e.g., ascertain whether the response is normal or depressed) of immune cells from patients suffering from disease, or to measure the motility of sperm for infertility patients.

Traditionally, the most popular assays for measuring cellular chemotaxis have utilized a so-called "Boyden chamber" (Boyden, 1962), or similar apparatus, in which the cells migrate through a filter that has pore openings that are smaller than the cell diameter. Typically, cells of a particular type are placed in a chamber on one side of the filter and a chemotactic agent is placed in a chamber on the other side. Results are usually quantified by counting the number of cells that have migrated through the filter. While such techniques are reasonably simple and widely available, they are associated with certain disadvantages. For example, they typically require a large number of highly purified cells. Isolating the cells, setting up the apparatus, and counting the cells which have migrated can be very labor intensive. Frequently, the process of isolating the cells can require several hours. Moreover, the cells are sometimes damaged during the process. For rare cell types, of course, the task of isolating a sufficiently large number of cells for use in the assay can be especially difficult and time consuming.

With most conventional chemotaxis assays, the process of examining and counting the cells that have moved has also been tedious and time-consuming. This is particularly true for assays that have relied upon manual examination, counting and analysis. Although some chemotaxis assays have automated, to varying degrees, these processes, they have not been entirely satisfactory either. For example, certain chemotaxis assays have employed automated readers of the type that detect the bulk amount of radiation emitted from a sample, e.g., a densitometer, fluorimeter, or spectrophotometer. While useful for determining the overall number of labeled cells in a region, such devices are not able to provide information regarding the positions of individual cells. Thus, it is not possible to image or map individual cells using such devices.

As another disadvantage, conventional cell-motility assay devices are not capable of simultaneously processing a large number of separate samples. In fact, most of the known assays accommodate only a single sample at a time. Of course, in situations where it is desirable to assay numerous samples in a relatively short time period, e.g., certain commercial research and clinical labs, the limited capacity of the known assay devices, which places a ceiling on throughput and productivity, can be a serious problem. Although a few multiple-site assays have been developed that can accommodate a plurality of samples at once, the total number of samples that can be simultaneously assayed is typically quite limited (e.g., less than 100). Moreover, the known multiple-site assays continue to suffer the disadvantages discussed above, e.g., their set-up and operation are tedious and labor-intensive, and they are not capable of providing positional information on individual cells.

SUMMARY OF THE INVENTION

One aspect of the invention provides an apparatus for assaying motility in response to a selected chemotactic agent. According to one embodiment, the apparatus includes a chamber having first and second side regions. Structure is provided facilitating the establishment of a concentration gradient of the chemotactic agent which increases on progressing from the first side region to the second side region. An optical system is provided for detecting selected individual cells in an interrogation region of the chamber. The apparatus further includes means for assigning positions to individual detected cells in the interrogation region in electronic readable form (e.g., by a digitization means). A programmed computing device is provided for comparing the distribution of detected, position-assigned cells in the interrogation region at two or more spaced time intervals.

In one embodiment, the computer means functions to compare the total number of detected cells whose positions are within the interrogation region at each of the spaced time intervals. In another embodiment, the computer means functions to (i) calculate a motion vector in the direction of the concentration gradient for each of the detected cells in the interrogation region, over the spaced time interval, and (ii) determine an average motion vector from the calculated individual vectors of the detected cells in the interrogation region.

According to one embodiment of the invention, the optical system includes an illumination source for directing a beam of light toward the chamber. Structure is provided to permit relative motion between the chamber and the beam of light for causing the beam to sequentially scan the area forming the interrogation region.

According to another embodiment, wherein the apparatus of the invention is used to detect fluorescent-labeled cells, the chamber is adapted to hold a cell-suspension liquid to a selected depth. Further, the optical system has a fluorescence excitation light source whose beam is adapted to be focused at a depth in the chamber that is intermediate the selected depth.

In one embodiment of the invention, the chamber is a capillary of substantially rectangular cross-section, having a first inlet proximate the first side region and a second inlet proximate the second side region.

In another embodiment, the chamber includes a plurality of separate sample wells positioned along the first side region.

Another aspect of the invention provides an apparatus for determining the motile response to a given chemotactic agent of a selected type of cell contained in a sample of mixed cell types. According to one embodiment, the apparatus includes a chamber having a first side region adapted to receive the mixed-cell sample and an opposed, second side region. Structure is provided facilitating the establishment of a concentration gradient of the chemotactic agent which increases on progressing from the first side region to the second side region. The apparatus further includes means for discriminating individual cells of the selected type from other components contained in the mixed-cell sample, as well as means for detecting and mapping the positions of individual cells of the selected type in a region between the first and second side regions.

According to one embodiment, the means for discriminating individual cells of the selected type includes a fluorescent reporter capable of selectively binding to the individual cells. In this embodiment, the fluorescent reporter is of a type having wavelengths of excitation and emission that minimize optical interference in the sample. In a related embodiment, the means for detecting and mapping the positions of individual cells includes an illumination source for directing an excitation beam of light toward the chamber. In this embodiment, the excitation beam has a wavelength that minimizes optical interference from components in the unpurified sample other than the selected type of cell.

According to one embodiment, the means for detecting and mapping the positions of individual cells further includes a focusing lens positioned proximate the chamber. The focusing lens is configured to focus the beam of light to a beam spot in the interior of the chamber. A light collector is positioned proximate the chamber. The light collector is configured to gather fluorescent emission leaving the chamber and to transmit the fluorescent emission away from the chamber in a retrobeam. A photodetector is spaced apart from the chamber along the pathway of the retrobeam and is responsive to the retrobeam. A spatial filter is positioned between the light collector and the photodetector. The spatial filter is disposed to intercept the retrobeam. Further, the spatial filter is configured to admit only a portion of the retrobeam to the photodetector.

In one embodiment, the chamber is a capillary of substantially rectangular cross-section. The capillary is provided with a first inlet proximate the first side region and a second inlet proximate the second side region. Another embodiment provides a plurality of chambers disposed on a single substrate. According to a further embodiment, each of the chambers includes a plurality of separate sample wells positioned along the first side region.

A further aspect of the invention provides a method of determining the motile response to a given chemotactic agent of a selected type of cell contained in a sample of mixed cell types. According to one embodiment, the method includes the steps of (i) labeling the selected type of cell contained in the mixed-cell sample with a fluorescent compound capable of preferentially binding to the selected type of cell, the fluorescent compound having wavelengths of excitation and emission that minimize optical interference from components in the sample other than the selected type of cell; (ii) establishing a concentration gradient of a chemotactic agent proximate the sample such that the concentration progressively increases in a direction away from the sample; (iii) directing an excitation beam of light along a region of the concentration gradient, the excitation beam having a wavelength that minimizes optical interference from components in the sample other than the selected type of cell; (iv) detecting areas of peak fluorescence representative of the selected type of cell in the sample; (v) identifying the positions of individual cells of the selected type of cell along the region; and (vi) analyzing the positions of the selected type of cell to determine the motility of the selected type of cell.

According to one embodiment, steps (iii) to (v) are repeated on at least two, temporally-spaced occasions.

In one embodiment, a plurality of different samples are analyzed to determine the motility of the selected type of cell in a substantially parallel fashion upon a single substrate. A related embodiment provides the additional steps of (i) selecting a plurality of cell types and labeling each of the plurality of selected cell types with a unique fluorophore; and (ii) determining the motility of each of the plurality of selected cell types upon a single substrate in a substantially parallel fashion.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which identical reference numerals identify similar elements, and in which.

DETAILED DESCRIPTION OF THE INVENTION

One aspect of the present invention provides an apparatus for assaying cellular motility in response to a concentration gradient of a chemotactic agent. Generally, the apparatus includes a chamber having a region for receiving a biological sample containing cells of interest and a region for receiving a chemotactic agent. Adjacent or near the sample-receiving region, a concentration gradient of chemotactic agent is established. The apparatus further includes a motility scanner for detecting and mapping the positions of cells responsive to such concentration gradient. Means for processing and analyzing the collected data are also provided.

As used herein, the term "chemotactic agent" refers to both chemoattractants and chemorepellents.

I. Motility Chamber

A. Capillary Apparatus

Figure 1A:
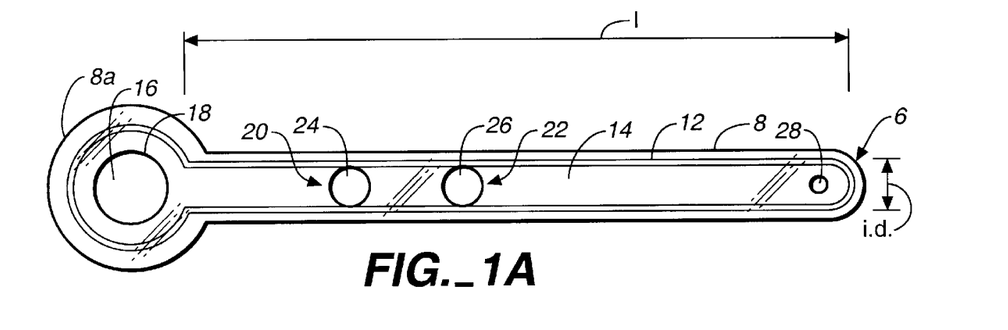
FIG. 1A is a top plan view of a motility assay chamber constructed in accordance with an embodiment of the present invention.
Figure 1B:
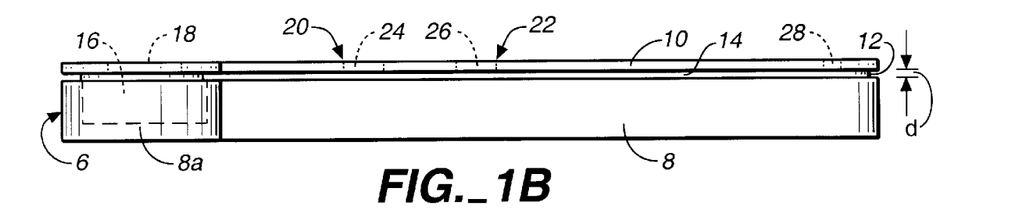
FIG. 1B is a side elevational view of the motility assay chamber of FIG. 1A.
Figure 1C:
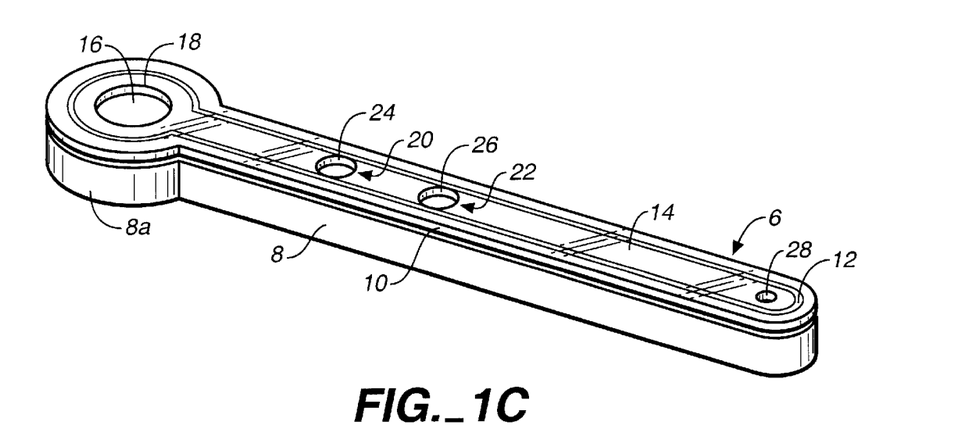
FIG. 1C is a perspective view of the motility assay chamber of FIGS. 1A–B.

FIGS. 1A–C show, in top, side and perspective views, respectively, a motility assay chamber according to an embodiment of the invention. In the illustrated embodiment, a capillary, indicated by the reference numeral 6, forms the assay chamber. Capillary 6 is constructed of two parts, an elongated base member 8, having an expanded head portion 8a at one end, and a cover plate 10 having substantially the same peripheral shape as base member 8, A continuous, narrow ridge 12 runs along the uppermost surface of base member 8, mimicking the base member's peripheral shape. Throughout its length, ridge 12 projects upwardly from the base member's upper surface to a uniform height. Cover plate 10 is sealed, in a liquid-tight manner, to the top surface of ridge 12. The area bounded by ridge 12 and the confronting faces of base member 8 and cover plate 10 defines an elongated lumen 14 extending most of the length of capillary 6.

A cylindrical well 16, formed in the head portion 8a of base member 8, extends from the base member's upper surface downward about halfway of the base member's depth. Above well 16, a circular passageway 18, having a diameter slightly less than that of well 16, extends through cover plate 10, permitting external access to well 16. At its end proximate the base member's expanded head portion 8a, lumen 14 opens directly into an upper region of well 16. At its other end, lumen 14 is vented by way of a small hole 28 traversing cover plate 10.

Lumen 14 has a rectangular cross section with a shorter dimension defining an interior depth of about 50 to 200 $\mu$m and a longer dimension defining a width of about 1 to 4 mm. The minimum length of the lumen is chosen to provide a desired distance between a sample of cells for motility analysis, placed in one area of the capillary, and a chemotactic agent, placed in another area of the capillary. In one embodiment, the length dimension of lumen 14, denoted in FIG. 1 by the letter "l," measures 5 cm; the inner diameter of the lumen, denoted as "i.d.," measures 3 mm; and the lumen depth, denoted as "d," measures 100 $\mu$m.

Lumen 14 has a first side region, denoted as 20, whereat a sample of cells may be deposited, and a second side region, denoted as 22, whereat a chemotactic agent may be placed. A first inlet, indicated by the numeral 24, extends fully through cover plate 10 above the first side region 20, permitting injection of a sample of cells into the capillary lumen. A second inlet, indicated by the numeral 26, extends fully through cover plate 10 above the second side region 22, permitting injection of a chemotactic agent into the capillary lumen. In one embodiment, the first and second inlets are separated by a distance of about 4–5 mm.

As discussed more fully below, an optics system, located outside of capillary 6, observes cellular motility occurring in the capillary lumen 14 through the cover plate 10. Accordingly, cover plate 10 is preferably constructed of a transparent material permissive of such observation, e.g., a high quality glass, such as that sold under the trade name "PYREX® code 7740" from Corning Corp. (Corning, N.Y.) or under the trade name "DURAN® 8330" from Schott Glass Technologies, Inc. (Duryea, Pa.). Other suitable materials for the capillary include acrylic, such as "Plexiglas® VS-UVT" available from AtoHaas Americas (Philadelphia, Pa.), and polystyrenes, such as "Styron 663" available from the Dow Chemical Company (Midland, Mich.).

Base member 8 may be constructed, for example, of a plastic or like material, e.g., acrylonitrile butadiene styrene (ABS), polystyrene or polymethyl methacrylate. ABS suitable for manufacture of the base member is available from BASF Corp. (Wyandotte, Mich.) under the trade name "TERLUX 2802 TR."

In one embodiment, not shown, a plurality of separate, elongated lumens are formed in a single base member. Additionally, the periphery of the base member may be configured to optimize the number of such units that can be loaded onto a stage or carousel in a motility scanner. For example, several triangle-shaped base members, each supporting one or more elongated capillary lumens, may be arranged side-by-side, forming a circle, on a rotatable carousel. Rotation of the carousel may then bring each lumen, in turn, into view for observation by an appropriate optics system.

As indicated above, in using the apparatus of the invention, a concentration gradient of chemotactic agent will be established near the cell sample. Together, inlet 26, second side region 22, as well as capillary lumen 14 provide a means for establishing a concentration gradient of a chemotactic agent. In this regard, it should be appreciated that upon injecting a diffusable chemotactic agent through inlet 26 into the capillary lumen 14, the agent will spread out, thereby establishing a gradient of chemotactic agent between the two side regions, 20 and 22, which increases on progressing from the first side region 20 to the second side region 22.

Generally, the concentration gradient should be smooth over this region. A gradient of such quality can be achieved by ensuring that establishment of the gradient is primarily diffusion-driven, without substantial influence by other forces, such as gravity. To this end, one embodiment of the invention provides a material in the lumen of the capillary that permits spreading of the chemotactic agent by diffusion, but prevents spreading by other forces. Specifically, the capillary lumen may be coated and/or filled with a material such as agarose, acrylamide, or other polymer material. Advantageously, such material may also serve to prevent movement of cells in the biological sample by means other than chemotaxis, e.g., by inadvertent jostling of the capillary.

The lumen of the capillary may also be coated or filled with any of the following materials, as desired: (i) an appropriate growth media for the cell sample of interest; and/or (ii) chemotaxis substrates like laminin, fibronectin, collagen, or others, as appropriate for the cell type(s) of interest.

B. Multi-Site, High-Throughput Assay Apparatus

Additional embodiments of the invention contemplate an assay apparatus having a great number of separate assay chambers. For example, certain embodiments provide plural assay chambers on a single substrate or supporting plate, with each assay chamber having a side region with one or more sample wells, or subchambers, and another side region for receiving a chemotactic agent. Means are provided for establishing a concentration gradient of the chemotactic factor which increases on progressing from the side region whereat the sample is received toward the side region whereat the chemotactic agent is received.

Figure 2A:
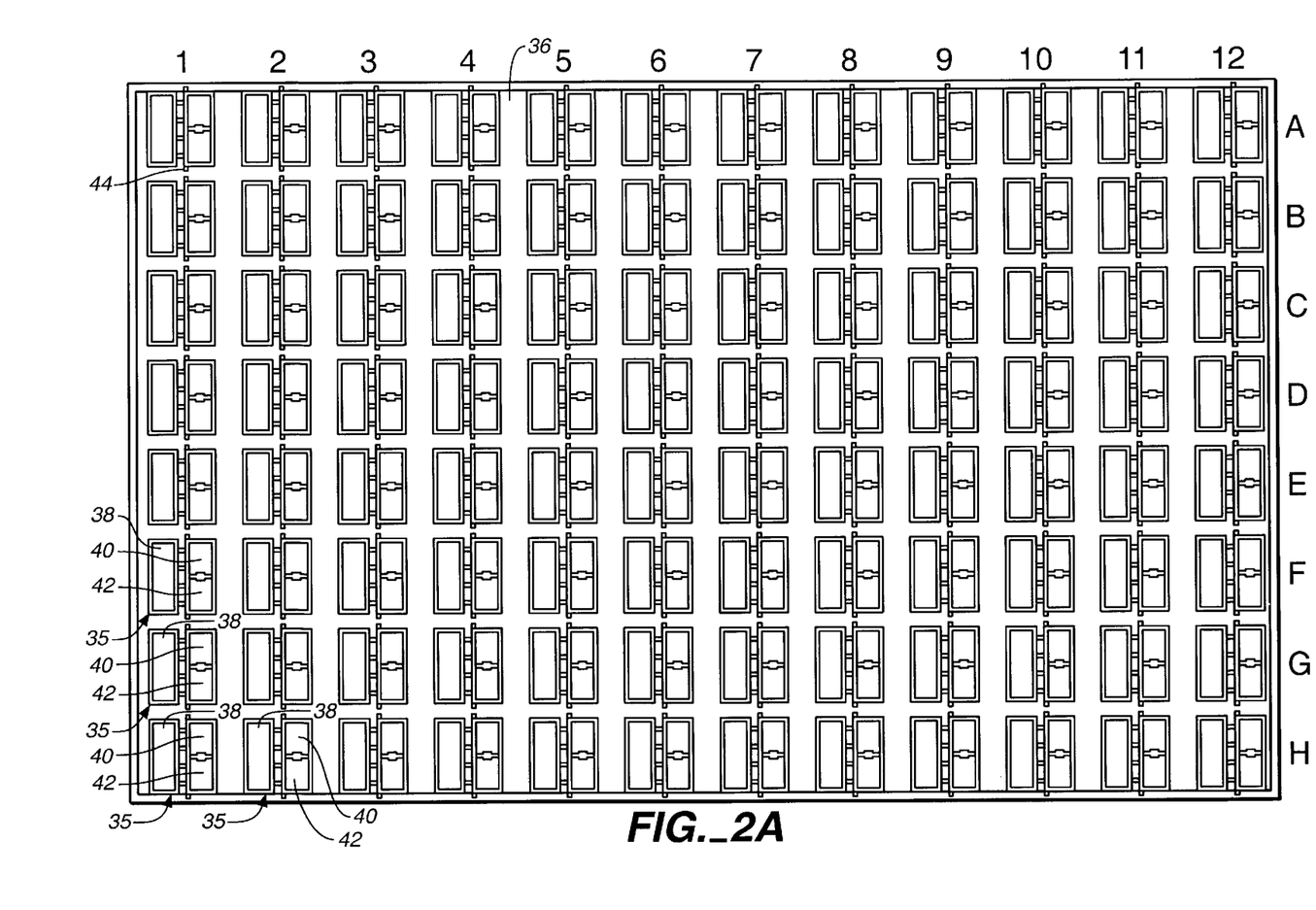
FIG. 2A is a partially schematic, top plan view of a high-throughput array of motility assay chambers disposed on a single substrate in accordance with an embodiment of the present invention.
Figure 2B:
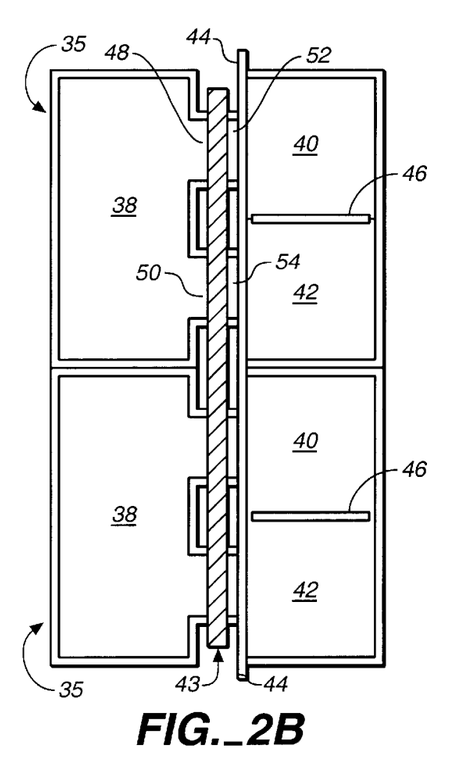
FIG. 2B is a partially schematic, top plan view of a pair of adjacent motility-assay chambers, from the array of chambers shown in FIG. 2A.

With reference now to FIGS. 2A and 2B, an embodiment of a high-throughput assay apparatus is shown. The high-throughput apparatus incorporates multiple assay chambers, or test sites, as indicated generally at 35, on a common substrate or supporting plate, denoted by the numeral 36. In the illustrated embodiment, each individual test site includes, along one side region thereof, a pair of adjacent wells, such as wells 40 and 42, opposing a larger well disposed at the other side region, such as well 38. Well 38 is separated from the pair of adjacent wells, 40 and 42, by an intervening interrogation zone, such as 43, and a thin, porous membrane, as denoted by the numeral 44. In an alternative embodiment (not shown), instead of a membrane, a small capillary coated or filled with a material such as agarose, acrylamide, or similar polymer materials, and/or cell culture media separates each sample well from an opposing attractant well.

Each well 40, 42 is configured to receive and hold a fluid sample containing cells of interest. Well 38 is configured to receive a chemotactic agent in a manner allowing for the establishment of a concentration gradient thereof between the sample wells 40, 42 and the attractant well 38, as described more fully below.

Attractant well 38 has a pair of openings, such as 48 and 50, extending through its face confronting sample wells 40, 42. Similarly, each sample well 40, 42 is provided with an opening, such as 52 and 54 (FIG. 2B), respectively, through its face opposite attractant well 38. It should be noted that each one of the openings, 48, 50, of attractant well 38 is disposed directly across from an opening, 52, 54, of a respective sample well. Together, the attractant well 38, the openings 48, 50 of attractant well 38, and the intervening area between attractant well 38 and sample wells 40, 42, provide a means for establishing a concentration gradient of a chemotactic agent. In this regard, it should be appreciated that a diffusable chemotactic agent placed in the attractant well will spread outward to establish a concentration gradient increasing in the direction extending from the sample wells to the attractant well. Motile cells placed in the sample wells may then migrate out in the direction of increasing attractant concentration.

As previously described, each sample well opening, such as 52, 54, is covered with a thin, porous membrane, such as 44. In one embodiment, membrane 44 stretches laterally across the support plate 36, covering the openings of at least two adjacent sample wells. The membrane 44 should be of a thickness and porosity to hold non-motile cells in the sample wells, while allowing motile cells to crawl out. For testing samples such as whole blood, a suitable membrane is about 8 $\mu$m thick with a pore diameter of about 8 $\mu$m. It should be recognized that other membrane pore diameters and membrane thicknesses might be utilized, depending upon the nature and sizes of the motile cells contained in a sample of interest. Generally, the membrane pore diameter should be slightly smaller than the diameter of the motile cells in the sample. By such an arrangement, motile cells can crawl through the pores to migrate out of a sample well, but the pore size does not permit the cells of interest to move out of the sample well by mere flowing or diffusion.

Figure 3A:
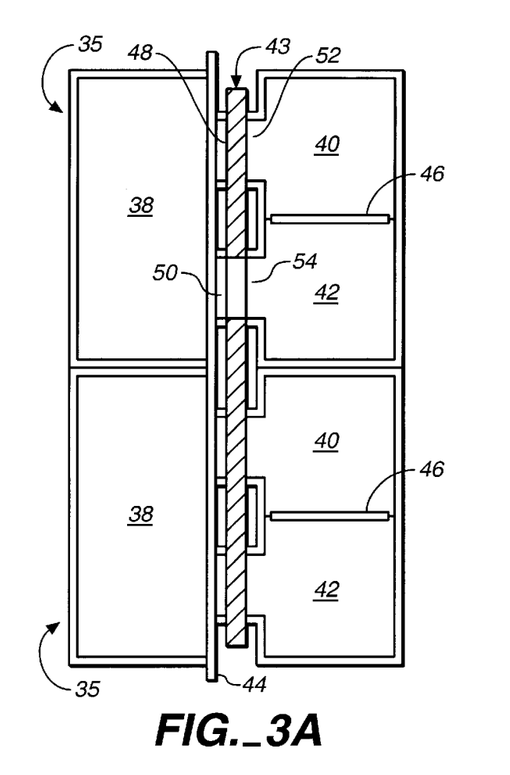
FIG. 3A is a partially schematic, top plan view of a pair of adjacent motility-assay chambers, adapted for use in a high-throughput array similar to that of FIG. 2A, in accordance with a further embodiment of the invention.
Figure 3B:
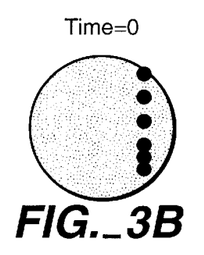
FIGS. 3B–F are schematic representations depicting the positions and movement of six individual cells, at consecutive, 30-minute intervals, subsequent to exposure to a concentration gradient of a chemotactic agent established across an interrogation zone of the motility-assay chamber of FIG. 3A.
Figure 3C:
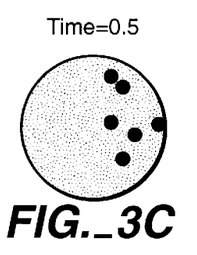
Figure 3D:
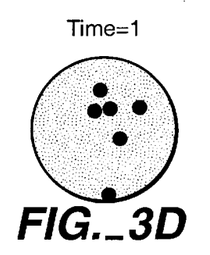
Figure 3E:
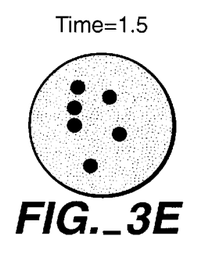
Figure 3F:
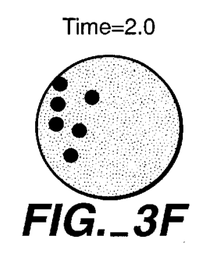

In an alternative embodiment, illustrated in FIG. 3A, the membrane 44 covers the openings 48, 50 of the attractant well 38 instead the sample-well openings 52, 54 as in the previous embodiment. Whereas the previous embodiment is particularly advantageous for population-based, cell-motility studies, this embodiment is especially useful in following the motility of individual cells. It is important, in this embodiment, to utilize a membrane 44 that will not present any significant impediment to diffusion of the chemotactic agent. Equally important, the membrane should be effective to prevent spreading of the chemotactic agent by forces other than diffusion, e.g., gravity. A thin, porous membrane, e.g., about 10–15 $\mu$m thick with a pore diameter of about 8 $\mu$m, should be suitable for such purposes.

In a further embodiment (not shown), particularly useful for population-based, cell-motility studies, two separate membranes are employed at each test site. Specifically, a first membrane covers the openings of the sample wells (e.g., such as that illustrated and described with respect to FIGS. 2A–B) and a second membrane covers the openings of the attractant wells (e.g., such as that illustrated and described with respect to FIG. 3A).

At this point, it should be noted that any arrangement that promotes meeting/mixing of the sample and chemotactic agent by diffusive forces only, preventing significant influence by other forces (e.g., gravity), may form a part of the invention. The above-described porous membranes and polymers, separating the sample wells and the attractant wells, are exemplary arrangements suitable to serve this purpose.

While the various test sites may be provided on a substrate or supporting plate of virtually any size and composed of any suitable material, one embodiment of the present invention contemplates using a supporting plate of a standard size, which can be constructed using conventional materials and means. Thus, in this embodiment, an injection molded rectangular plastic plate, the length and width of which conform to the commonly used standard of 5.030"×3.365" (127.76 mm and 85.47 mm), is preferred. Similarly, while a single plate may support any reasonable number of test sites, constructions corresponding to the commonly used "96-well" microtiter plate format are preferred. Thus, in the embodiment of FIG. 2A, an 8×12 array of test sites is situated on a 127.76 mm×85.47 mm injection molded rectangular plastic support plate. The position and spacing of the test sites on the support plate may be of standard spacing, e.g., 9 mm center to center. Utilization of standard outside dimensions for the plate frame, as well as standard spacing for the test sites on the plate, facilitates use of the plates with existing equipment, such as automated dispensers or optical readers, if desired.

Exemplary dimensions for the various test-site components laid out on a single 127.76 mm×85.47 mm support plate are as follows. Along the 127.76 mm dimension of the plate, each well, 38, 40 and 42, may have a sectional width of about 3 mm; and the interrogation lane 43, which represents the distance between the attractant well 38 and the sample wells 40, 42, may be about 1 mm wide. Thus, an exemplary overall width for an individual test site is about 7 mm. Along the 85.47 mm dimension of the plate, the test site may also measure about 7 mm. A partition, such as 46, between adjacent sample wells 40, 42, provides each sample well with a floor area of about 3 mm×3 mm. An 8×12 array of test sites is disposed on one surface of the plate, with adjacent test sites spaced 9 mm center to center.

Although the illustrated high-throughput embodiments show arrangements configured in accordance with the popular 96-well format, the invention also contemplates any other number of wells (e.g., 12, 24, 48, 384, 1536, etc.) disposed in any suitable configuration.

It should be appreciated that the apparatus of FIG. 2A is capable of handling multiple simultaneous and parallel assays. Specifically, 192 samples or aliquots can be assayed at the same time. For example, one sample well at each of the 96 test sites (i.e., 96 wells) could be filled with whole blood samples from 96 patients, these samples having been incubated with fluorescently-labeled antibodies specific for macrophage markers. The other sample wells (i.e., the remaining 96 wells) could be filled with whole blood samples from the same 96 patients, respectively, but these samples having been incubated with fluorescently-tagged antibodies specific for CD4-positive T-cell markers. A chemotactic chemical could then be placed in the various attractant wells, and a concentration gradient established between each attractant well and the opposing sample wells. Cell motility could then be observed in a substantially parallel fashion.

In one embodiment, the assay apparatus is designed for only a single use (i.e., it is disposable). Thus, every assay is performed in a clean apparatus.

C. Multi-Site, Ultra-High-Throughput Assay Apparatus

Figure 4A:
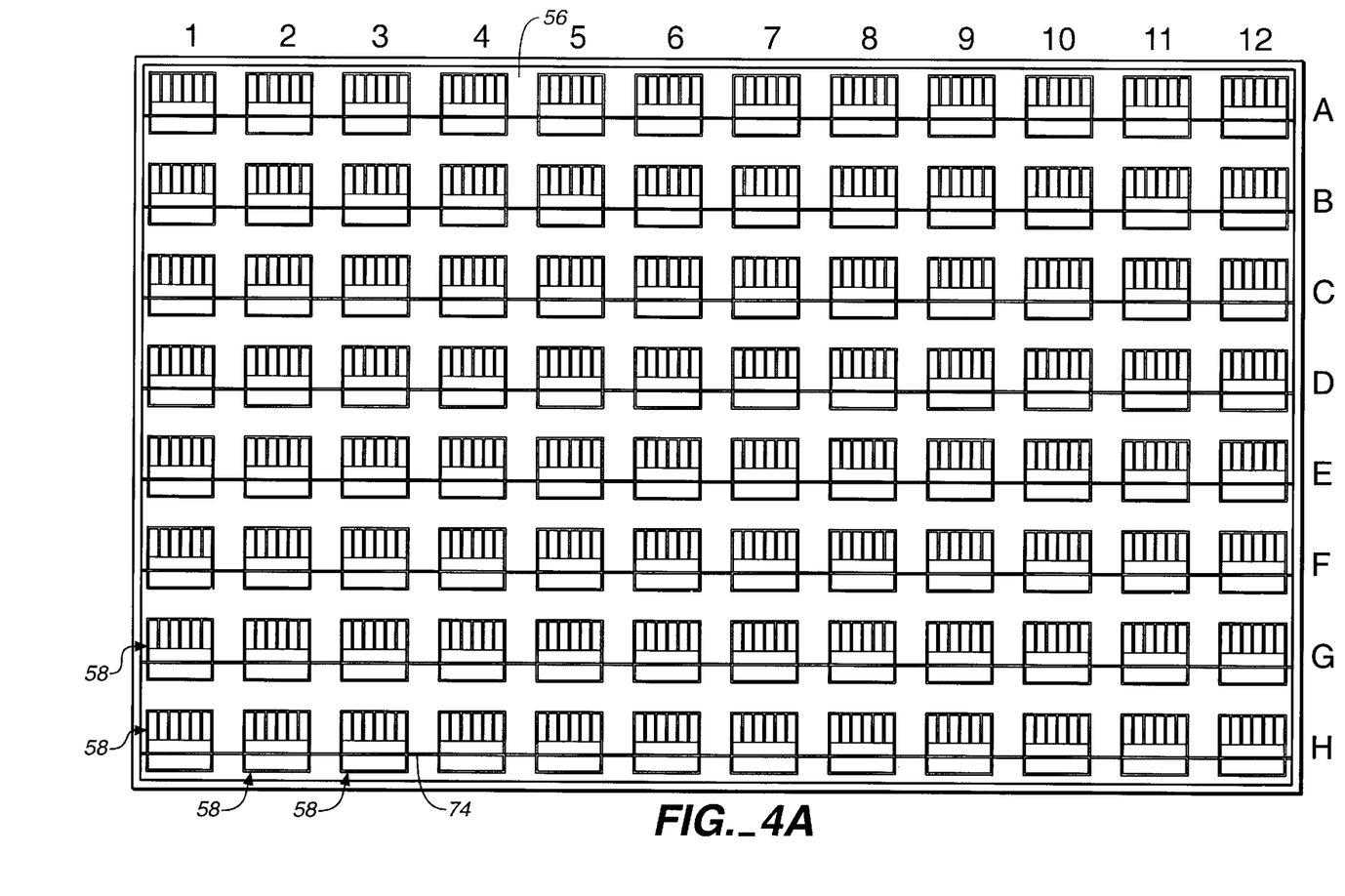
FIG. 4A is a partially schematic, top plan view of an ultra-high-throughput array of motility assay chambers disposed on a single substrate in accordance with an embodiment of the present invention.
Figure 4B:
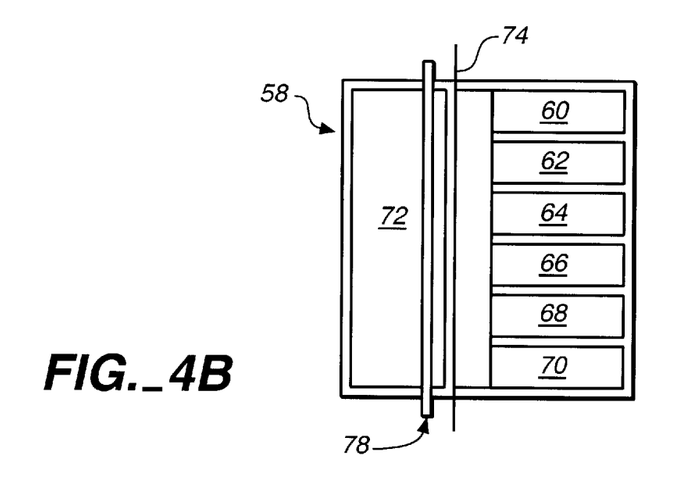
FIG. 4B is a partially schematic, top plan view of a single motility-assay chamber, from the array of chambers shown in FIG. 4A.
Figure 4C:
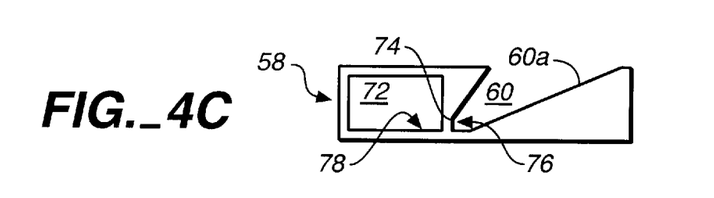
FIG. 4C is a partially schematic, side sectional view of a single motility assay chamber from the array of chambers shown in FIG. 4A.

Other embodiments of the invention contemplate multiple test sites disposed on a single substrate, with each test site having three or more sample wells or subchambers disposed adjacent means for establishing a concentration gradient of a chemotactic factor. One embodiment of such an ultra-high-throughput apparatus is depicted in FIGS. 4A–C. In the illustrated embodiment, six separate sample wells, such as 60, 62, 64, 66, 68, and 70, are disposed across from an attractant well 72 at each of multiple test sites, such as sites 58. Each of the sample wells has an opening, such as opening 76 of well 60 (FIG. 4C), through its wall facing the attractant well 72. A porous membrane 74, which extends longitudinally across the supporting plate 56, covers the openings 76 of several adjacent sample wells. As with the previous embodiment, a suitable membrane for certain cell types, e.g., whole blood, is about 8 µm thick and has 8 µm pores. An interrogation zone, indicated in FIG. 4B by the reference numeral 78, extends the length of the attractant well 72, running parallel, and in proximity to, the membrane 74. The interrogation zone 78 provides a region, about 1 mm in width, along which cell motility may be observed.

Together, attractant well 72 and the intervening area between attractant well 72 and the sample wells 60, 62, 64, 66, 68, 70 provide a means for establishing a concentration gradient of a chemotactic agent. In this regard, it should be appreciated that a diffusable chemotactic agent deposited within, and along the length of, the attractant well will spread outward to establish a concentration gradient increasing in the direction extending from the sample wells to the attractant well. Motile cells placed in the sample wells may then migrate out in the direction of increasing attractant concentration.

As indicated above, an ultra-high-throughput apparatus, as contemplated herein, will have numerous test sites, or assay chambers, situated upon a single support plate 36. In this regard, one embodiment contemplates an 8×12 array of test sites situated on a 127.76 mm×85.47 mm injection molded rectangular plastic support plate. The length and width of each test site measures approximately 7 mm×7 mm.

In the embodiments of the present invention employing a support plate or substrate of relatively limited dimensions (e.g., the size of a standard microtiter plate), with such plate or substrate having a large number of test sites situated thereon, it should be appreciated that the sample wells or subchambers may be relatively small, accommodating, for example, only about 3 µl of fluid sample or less.

Accordingly, it may be advantageous to configure the floor of each sample well, such as floor 60*a* of well 60 (FIG. 4C), with a downward slope towards the interrogation area 78. This construction should help to ensure that the sample will be positioned in the sample well proximate the membrane 74 so that motile cells will have an opportunity to sense the nearby chemotactic agent and migrate up the concentration gradient.

It should be appreciated that the apparatus of FIGS. 4A–C is capable of handling a great number of simultaneous and parallel assays. Specifically, 576 samples (i.e., 6 separate samples at each of 96 test sites) can be assayed at the same time. For example, 96 different blood samples, each from a unique source, could each be divided into six aliquots, and each aliquot then incubated with fluorescently-labeled antibodies specific for a particular cell type. The samples could then be loaded into the sample wells of 96 respective test sites on a single substrate. For example, at one test site: (i) one well could contain a sample aliquot which has been incubated with fluorescently-labeled antibodies specific for neutrophils, (ii) a second well could contain a sample aliquot which has been incubated with fluorescently-labeled antibodies specific for macrophages, (iii) a third well could contain a sample aliquot which has been incubated with fluorescently-labeled antibodies specific for eosinophils, (iv) a fourth well could contain a sample aliquot which has been incubated with fluorescently-labeled antibodies specific for CD8-positive T-cells, (v) a fifth well could contain a sample aliquot which has been incubated with fluorescently-labeled antibodies specific for CD4-positive T-cells, and (vi) a sixth well could contain a sample aliquot which has been incubated with fluorescently-labeled antibodies specific for basophils. The various sample aliquots could then be exposed to a concentration gradient of a chemotactic agent established by placing the chemotactic agent in an opposing attractant well and permitting it to diffuse outward toward the sample cells. Cell motility could then be observed in a substantially parallel fashion.

D. Multi-Site, Ultra-High-Throughput Under-Agarose Apparatus

Figure 5A:
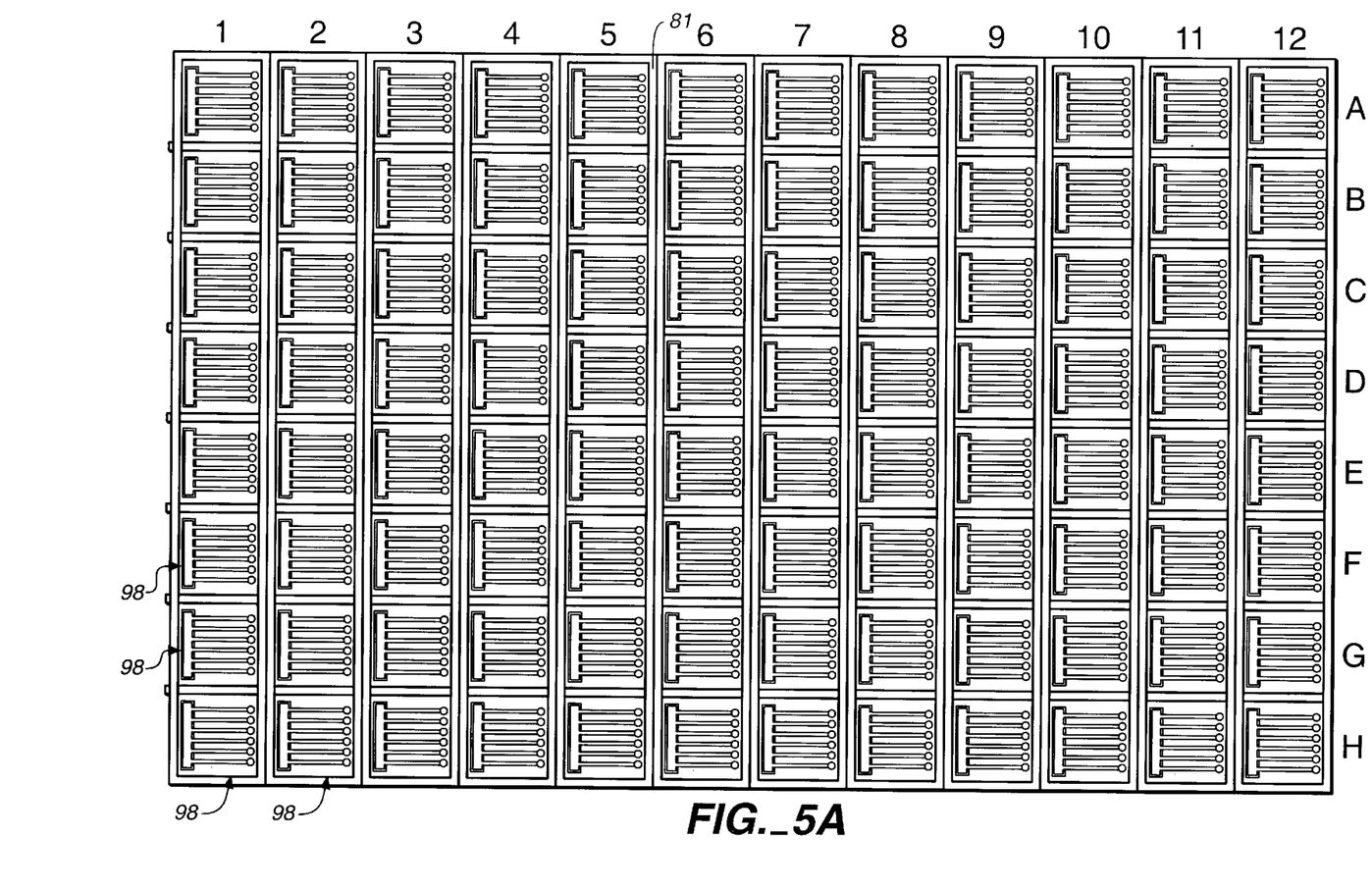
FIG. 5A is a partially schematic, top plan view of an ultra-high-throughput array of motility array chambers disposed on a single substrate in accordance with a further embodiment of the present invention.
Figure 5B:
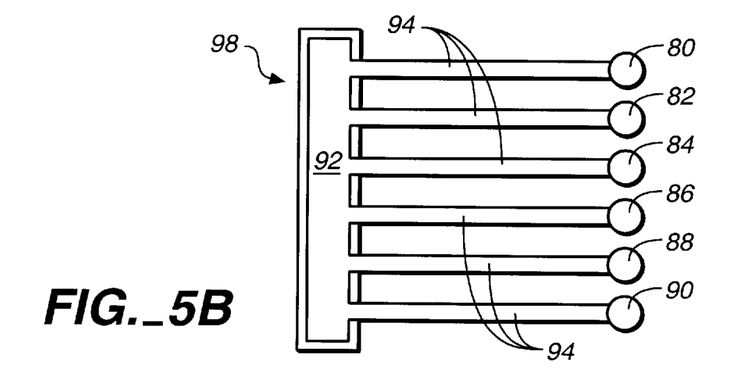
FIG. 5B is a partially schematic, top plan view of a single motility-assay chamber, from the array of chambers shown in FIG. 5A.

A further embodiment of an ultra-high-throughput apparatus, in accordance with the present invention, is depicted in FIGS. 5A–B. Similar to the embodiment of FIGS. 4A–C, this embodiment includes six separate sample-receiving wells, or subchambers, such as subchambers 80, 82, 84, 86, 88, and 90, shown in FIG. 5*b*. Also similar to the previously-described ultra-high-throughput apparatus, a well or subchamber for receiving a chemotactic agent, such as subchamber 92, is situated across from the sample-receiving subchambers. The embodiment of FIGS. 5A–B differs from the previous embodiment, however, in the means separating the attractant subchamber 92 from the sample subchambers 80, 82, 84, 86, 88, 90. As illustrated, a capillary, such as 94, is interposed between each sample subchamber 80, 82, 84, 86, 88, 90 and the attractant subchamber 92. Each capillary is disposed to communicate its respective sample subchamber with the opposing attractant subchamber.

Together, the attractant subchamber 92 and the lumens of the various capillaries 94, communicating the attractant subchamber 92 with the sample subchambers 80, 82, 84, 86, 88, 90, provide a means for establishing a concentration gradient of a chemotactic agent. In this regard, it should be appreciated that a diffusable chemotactic agent deposited within, and along the length of, the attractant subchamber will spread outward through the various capillaries to establish a concentration gradient increasing in the direction extending from the sample subchambers to the attractant subchamber. Motile cells placed in the sample subchambers may then migrate out in the direction of increasing attractant concentration.

In one embodiment, each capillary is formed integrally with its respective sample subchamber, the latter comprising an enlarged semi-hemispherical well at one end of the capillary. Additionally, the lumen of the capillary, between the sample subchamber and the attractant subchamber, is filled with agarose and/or cell-culture media. Diffusion of the chemotactic agent from the attractant subchamber through the capillary-filling material is permitted. Likewise, cellular movement through the capillary toward the attractant subchamber by way of crawling is permitted. However, movement of cells by mere flowing or diffusion is blocked.

As with the previously described ultra-high-throughput apparatus, the embodiment of FIGS. 5A–B has numerous test sites, such as sites 98, situated upon a single support plate 36. In this regard, one embodiment contemplates an 8×12 array of test sites situated on a 127.76 mm×85.47 mm injection molded rectangular plastic support plate, the length and width of each test site measuring approximately 7 mm×7 mm.

It should be appreciated that the apparatus of FIGS. 5A–B is capable of handling a great number of simultaneous and parallel assays. Specifically, 576 samples (i.e., 6 separate samples at each of 96 test sites) can be assayed at the same time. For example, (i) neutrophils, (ii) macrophages, (iii) eosinophils, (iv) CD8-positive T-cells, (v) CD4-positive T-cells, and (vi) basophils could be simultaneously tested for responsiveness to a chemotactic agent at a single site; with 96 such tests being carried out in parallel at different sites situated on a single support plate.

E. Motility Assay For Determining Responsiveness to Chemorepellents

While the above-described embodiments have primarily been described in connection with chemoattractants, it should be noted that the invention contemplates determinations of cell motility responsive to chemorepellents, as well. In this regard, in an assay chamber having first and second side regions, both (i) a sample containing at least one cell type of interest and (ii) one or more chemorepellents could be placed at or along the same side region. For example, a cell sample and chemorepellent could be injected into the same receiving well or subchamber disposed at the first side region. It should be appreciated that, in such an arrangement, the concentration of chemorepellent would be greatest at or near the first side region and would decrease in a direction extending toward the second side region, e.g., along an intervening region or zone. Here, the first and second side regions and the intervening region or zone provide means for establishing a concentration gradient of a diffusable chemorepellent. An interrogation zone, e.g., adjacent or near the first side region and/or at or along the intervening region or zone, could then be observed to ascertain cells moving down the gradient.

At each test site, opposing wells or subchambers for separately receiving sample at one side region and chemotactic agent at a second side region would not be required. Rather, a single receiving well or subchamber (per tested sample or aliquot) at one of the two side regions would be sufficient, since both the cell sample and chemorepellent could be placed therein. The present invention, thus, contemplates multiple embodiments useful for determining cell motility responsive to one or more chemorepellents. In some embodiments, the apparatus has one or more wells or subchambers situated at both of two opposing side regions. Here, the wells or subchambers at one of the two side regions may or may not be used. In other embodiments, the apparatus has one or more wells or subchambers situated at only one of two opposing side regions. In these latter embodiments, one of the side regions lacks wells or subchambers.

It should be appreciated that the motility assay for determining responsiveness to chemorepellents may be configured as any of the previously described embodiments, e.g., providing one or a few test sites embodied in a capillary-type device, or many test sites in a high-throughput or ultra-high-throughput format on a single substrate plate.

II. Motility Scanner

Another aspect of the present invention provides a motility scanner for detecting and mapping the positions of individual cells in a selected region of the cell-motility chamber. In various embodiments, the motility scanner includes an optics system that interrogates the region with light and, by detecting light traveling away from the sample (e.g., passing through the sample, or emitted from the sample), distinguishes individual cells, one from another, that are present in the region at a particular time. With regard to the detection of cells, means are provided for assigning positions to individual cells, detected in the interrogation region, in electronic readable form. In one embodiment, a light-sensitive device having a plurality of light-sensitive cells, referred to as pixels, is responsive to light indicative of individual cells. For example, the light-sensitive device may be a charge-coupled device (CCD), or the like. Thus, the motility scanner is able to generate individual cell location information (e.g., as pixel maps, or sets of x, y coordinates) which can be stored in electronic readable form for further processing and analysis.

The region chosen for observation, referred to herein as an interrogation lane, region or zone, is an area adjacent the side region whereat a sample is deposited and along which migrating cells pass as they move up or down a concentration gradient of a chemotactic agent. For example, in embodiments of the invention where a stretch of capillary separates a sample-receiving region (e.g., a sample well or subchamber) from an attractant-receiving region (e.g. an attractant well or subchamber), an appropriate interrogation zone may comprise a window encompassing an intermediate region along such stretch of capillary. In embodiments of the invention where a thin, porous membrane separates a sample well or subchamber from an attractant well or subchamber, an appropriate interrogation zone could comprise a window encompassing a region beside the membrane, between the sample wells and the attractant well.

In one embodiment, an unpurified sample containing a cell type of interest is incubated with a staining agent that is differentially absorbed by various cell types. Individual, stained cells are then detected based upon color or intensity contrast, using any suitable microscopy technique(s), and such cells are assigned positional coordinates. In another embodiment, an unpurified cell sample is incubated with one or more detectable reporters, each reporter capable of selectively binding to a specific cell type of interest and imparting a characteristic fluorescence to all cells labeled therewith. The sample is then irradiated with the appropriate wavelength light and fluorescing cells are detected and assigned positional coordinates.

One skilled in the art will recognize that a variety of means for discriminating selected cells from other components in an unpurified sample are available. For example, these can include dyes, radioisotopes, fluorescers, chemiluminescers, beads, enzymes and antibodies. Dye compositions that differentially stain various types of leukocytes, permitting cell-type specific identification of cells in a unpurified sample of blood based upon the relative intensity of transmitted and/or emitted light are disclosed in U.S. Pat. No. 4,146,604, expressly incorporated herein by reference. Specific labeling of cell types can be accomplished, for example, utilizing fluorescently-labeled antibodies. The process of labeling cells is well known as is the variety of fluorescent dyes that may be used for labeling particular cell types. See, e.g., R. P. Haughland, "Handbook of Fluorescent Probes and Research Chemicals," Sixth Edition, Molecular Probes, Inc. (1996).

If desired, multiple cell types in a single sample could be labeled, each with one or more unique, cell-type specific reporters, and placed in a single sample well. In this way, a plurality of cell types could be tracked at one time along the same interrogation zone.

When it is desired to observe motile cells of a specific type in an unpurified sample, one embodiment of the invention contemplates, for use as the detectable label, a fluorescent compound having wavelengths of excitation and emission that minimize optical interference from components in the unpurified sample other than the chosen cells. Additionally in this embodiment, the illumination source used to excite the fluorescent compound should have a wavelength that minimizes optical interference from components in the unpurified sample other than the chosen cells. For example, U.S. Pat. No. 5,585,246, expressly incorporated herein by reference, discloses certain fluorescent dyes and excitation-beam wavelengths that minimize optical interference.

Optical interference is minimized by the use of a selectively binding staining agent that has an excitation and emission wavelength that minimizes absorption, autofluorescence, and diffraction by compounds within the sample preparation other than the detectable label on the binding agent.

The motility scanner includes a microscopy system that permits observations of cell positions in unfixed samples of cells. For example, phase-contrast microscopy, differential-interference-contrast microscopy, dark-field microscopy, confocal laser-scanning microscopy, and digital deconvolution microscopy are all suitable microscopy techniques.

Exemplary phase-contract microscopy systems, capable of identifying the positions of individual cells in a sample, are disclosed in U.S. Pat. Nos. 4,896,967 and 5,093,866, each expressly incorporated herein by reference.

Figure 6:
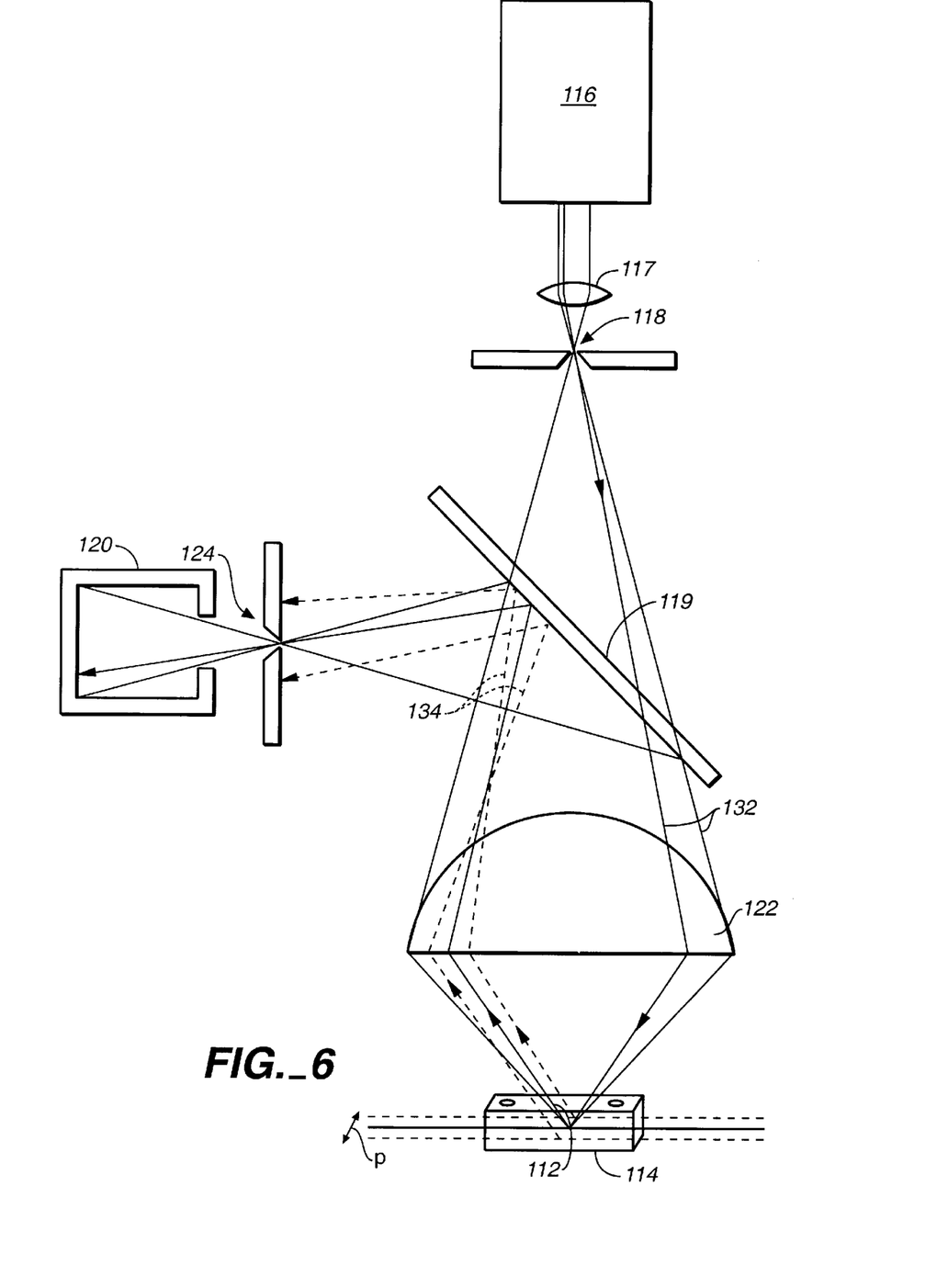
FIG. 6 is a schematic representation of a confocal imaging system in accordance with an embodiment of the present invention.

An exemplary confocal system includes the components illustrated in FIG. 6, wherein solid rays 132 represent in-focus light and dashed rays 134 represent out-of-focus light. The optical system at any instant focuses a beam spot 112 onto a single point at a specific depth in an assay chamber 114 containing the sample. For example, a laser 116, whose light has been conditioned by lens 117 to pass through a pinhole 118, can supply the appropriate illumination. In the illustrated arrangement, the light from laser 116 passes through a beam splitter 119 and is focused to a beam spot 112 by an objective lens 122. The fluorescence emitted from the illuminated material in the chamber is collected, by the same objective lens 122, and brought to an image at the entry port of a suitable light detector 120. A pinhole aperture 124 is placed at the detector 120 at the site that is confocal with the illuminating pinhole 118. Thus, light from the focal plane P in the specimen converges on the pinhole aperture 124 and enters the detector 120. By contrast, light from regions out of the plane of focus will fail to focus through the pinhole aperture 124 and, therefore, will be largely excluded from the detector 120.

Instead of focusing the beam spot to a single point at a specific depth, as illustrated in FIG. 6, the beam spot may be conditioned to encompass a columnar region within the chamber. Particular imaging instrument scanners capable of focusing a beam spot to a columnar region with an assay chamber are disclosed in U.S. Pat. Nos. 5,547,849, 5,556,764, and 5,585,246, each expressly incorporated herein by reference. Generally, such an imaging instrument having an objective lens, focuses a beam of laser light into a gausian waist that intersects the assay chamber. The gausian waist illuminates a columnar region in the chamber. As the illuminated columnar region passes through the chamber, the laser illumination excites fluorescent emission from fluorescent matter in the illuminated region whose excitation wavelength matches the wavelength of the illumination light.

The optical system matches a spatial filter to the objective lens such that only a portion of the light is admitted onto the detector. The lens used to focus the excitation beam into a gausian waist also serves a light collector for the fluorescent emission. Some of the fluorescent emission impinging upon the lens will be transmitted as a retrobeam to the detector optics. The combination of the focused gausian waist and the matched spatial filter/light collector enables this optical system to detect fluorescence from a container in a limited depth of field.

The fluorescence from the illuminated region can be detected by a light detector to produce a fluorescent emission signal. The emission signal is sampled periodically by a digitization means, e.g., a digital sampler, into a series of overlapping data samples in electronic readable form (digital). A chosen region of the chamber is observed in a raster-scanning fashion. Sampling circuitry, coupled to the scanner, generates scanned images of the material within the scanned region of the chamber (defined by the raster-scan dimensions and the depth of field).

An exemplary digital deconvolution microscopy system includes a video camera, standard white-light microscope, a computer, a cooled CCD camera, a light source, a z axis control, a framegrabber, as well as image acquisition software and deconvolution software. The digitization means capture and digitize the images from the microscope, which are then stored in electronic readable form (e.g., on the computer). Image enhancement algorithms are used to deconvolve the image, i.e. remove the blur or haze contributed by the out-of-focus image planes. An exemplary system is sold under the trademark PROTEUS™ by VayTek, Inc. (Fairfield, Iowa).

To build up a two-dimensional image, data from each point or columnar region in the focal region of the sample are collected sequentially by scanning across the field in a raster pattern. To this end, means are provided for effecting relative motion between the chamber and the beam of light thereby causing the beam to sequentially impinge the interior of the chamber in a two-dimensional array of beam spots. Such means can operate by (i) moving the illuminating beam and/or (ii) moving the sample. Embodiments of the invention contemplate, for example, the use of the following scanning arrangements: (i) a stage-scanning type, in which a stage supporting the specimen is moved in a scanning motion while the optics remain stationary; and/or (ii) a beam-scanning or mirror-scanning type, in which the illuminated point or column of light is scanned over the specimen. In one particular embodiment, scanning is accomplished by deflecting the beam with an oscillating mirror placed between a dichroic mirror and an objective lens in such a way that the illuminating light and the confocal type pinhole at the detector remain strictly in register.

In one embodiment, the means for providing relative motion between the chamber and the beam of light causes the beam spots to partially overlap each other. For example, to detect motile cells having diameter of about 8 µm and tagged with a known fluorescent label, an excitation beam spot about 4 µm in diameter could be raster scanned, in 2 µm steps, over the interrogation zone. Detected fluorescent emissions could be sent to a CCD camera to generate an image, comprised of a two-dimensional array of 4×4 µm pixels, showing cell locations in the scanned region.

In addition to confocal scanning systems, or the like, other detection means useful in ascertaining the motility of cells responsive to a concentration gradient of chemotactic agent include video microscopes, CCD-microscopes or other image capture devices. In one embodiment, cell behavior during the desired period of observation is recorded on VHS or Beta format videotape through a standard video camera positioned in the vertical ocular tubes of a trinocular compound microscope or in the body of an inverted microscope and attached to a high quality video recorder. The video recording is then played into a digitization means, e.g., a MACH Series™ PCI frame grabber, available from Data Translation (Marlboro, Mass.). The electronic readable (digitized) data is then accessed and processed by an appropriate dynamic image analysis system, such as that disclosed in U.S. Pat. No. 5,655,028, expressly incorporated herein by reference. Such a system is commercially available under the trademark DIAS® from Solltech Inc. (Oakland, Iowa). Software capable of assisting in discriminating cells from debris and other detection artifacts that might be present in the sample should be particularly advantageous.

It should be appreciated that, in addition to providing an assay useful for determining the motility of cells in purified samples (i.e., each sample substantially containing only a single, selected cell type), the present invention is also useful for carrying out motility determinations on unpurified samples (e.g. containing mixed cell types). This is a significant advantage over the prior motility assays that have generally been limited to purified samples.

It should also be appreciated that the chemotaxis assay of this invention can be used with a variety of cell types. Examples include, but are not limited to, lymphocytes, monocytes, neutrophils, basophils, macrophages, eosinophils, polymorphonuclear leukocytes, fibroblasts, endothelial cells, epithelial cells, neurons, tumor cells, motile gametes (e.g. sperm), motile forms of bacteria (e.g., the Gram-negative bacteria *Escherichia coli* and *Salmonella typhimurium*), and fungi (e.g. slime molds), among others.

Cells of a chosen type can be differentiated in a mixed-cell population, for example, using a detectable reporter or a selected combination of detectable reporters that selectively and/or preferentially bind to such cells. Labeling can be accomplished, for example, using monoclonal antibodies to selectively expressed CDs, antigens, receptors, and the like. Examples of tumor cell antigens include CD9, CD10, CD19 and CD20 present on B cell lymphoma cells; tumor cell antigens that are specific for certain breast tumors include Her2/Neu and estrogen receptors. See, e.g. Nasser Javadpour, "Tumor Marks, Biology and Clinical Applications," Praeger Publishers, New York (1987). Markers of leukocyte subpopulations include, for example, CD3, CD4, CD8, CD10, CD14, CD16, and CD20, among others. See, e.g. Janeway and Travers, "Immunobiology: The Immune System in Health and Disease," 2nd edition, Current Biology Ltd/Garland Publishing Inc. (1996), at Appendix I. One of skill in the art will appreciate that numerous sources are available (e.g. scientific literature, commercial catalogs, etc.) that identify various known cell markers. Moreover, additional markers are continually being discovered. Any such markers, whether known now or discovered in the future, that are useful in labeling cells may be exploited in practicing the invention.

Since few, if any, markers are absolutely specific to only a single type of cell, it may be desirable to label at least two markers, each with a different label, for each chosen cell type. Detection of multiple labels for each chosen cell type should help to ensure that the motility analysis is limited only to the cells of interest.

The chemotaxis assay of this invention can be used with a variety of chemotactic agents, including chemoattractants and chemorepellents. These include, but are not limited to, 'ELR'IL-8; GROα, β; Nap-2; ENA-78; IP-10; Mig; SDF-1α, β; MCP-1,2,3,4,5; eotaxin; LARC; MIP-1α, β; RANTES; TARC; I309; CCF18; lymphotactin; SCM-1; $CX_3C$ chemokine (fractalkine); the complement component C5a; arachidonate derivative leukotriene B4 ($LTB_4$); platelet activating factor (PAF); formylmethionyl peptides of bacterial origin such a formyl-met-leu-phe (fMLP); the neutrophil α granule protein CAP37; cAMP; folic acid; D-glucose; D-galactose; D-mannose; maltose; D-fructose; NaCl; $CaCl_2$; $MgCl_2$; follicular factors; IL-4; PDGF; fibronectin; EGF; TGF-β1; laminin; insulin; NGF; GABA; citrate; chlorinated benzenes; phosphate; alpha-methylaspartate; and macrophage inhibitor factor (MIF); among others. A sample or aliquot containing at least one cell type of interest may be assayed against a single chemotactic agent or any desired number of chemotactic agents in combination.

III. Data Analysis

After setting up a concentration gradient of a chemotactic agent near a sample of cells, an appropriate interrogation zone of the motility assay chamber is scanned. For example, FIGS. 3B–F schematically depict six individual cells under observation, at consecutive, 30-minute intervals, subsequent to exposure to a concentration gradient of a chemotactic agent established across a region of the motility-assay chamber of FIG. 3A. The positions of individual cells are observed and stored, e.g., as pixel images and/or x, y coordinates. Computer means are provided for processing and analyzing the data.

The collected data can be analyzed for purposes of (i) single-cell tracking and/or (ii) population tracking. With regard to single-cell tracking, individual cells are followed as they travel along their respective paths. With regard to population tracking, although the positions of individual cells are determined each time data is collected, individual cells are not followed along their respective paths. Rather, the individual cell positions are used to determine cell population behavior.

A dynamic image analysis system, suitable for use with the present invention, is disclosed in U.S. Pat. No. 5,655,028, expressly incorporated herein by reference. Such a system is commercially available under the trademark DIAS® from Solltech Inc. (Oakland, Iowa). Additional analysis systems, also expressly incorporated herein by reference, are taught by Chon, J. H., et al. (1997) and by Glasgow, J. E., et al. (1989).

Advantageously, tracking of no more than a few hundred individual cells per assay should provide adequate results for most purposes.

A. Single-Cell Tracking and Single Cell-Movement Parameters

For purposes of tracking the movement of single cells in an assay, the positions of individual cells in an interrogation zone are determined on several temporally-spaced occasions. For example, to determine the motility of leukocytes in a whole blood sample, successive "snap shots" of cell migration can be collected once about every 5–10 minutes over a period of about 1–4 hours. For other cells, such data might be collected once about every 1 hour over a period of about 1–2 days.

Several useful measurements, as set out in Table 1, can be made:

TABLE 1

| Measured Parameter | Definition of parameter |
|---|---|
| τ | the average length of time a cell tends to remain traveling along a straight path before changing direction |
| v | the root mean square speed of the cells |
| φ | 2f-1; where f is the fractional orientation factor and is 1 when the cell is traveling in the hemi-circle toward the chemoattractant source and is 0 when the cell is moving toward the hemi-circle away from the chemoattractant source |

Table 2, below, shows a flowchart for analysis of single cell measurements, leading to a determination of the net flux.

TABLE 2

| Step No. | Measurement/Calculation |
|---|---|
| 1 | Determine positions of individual cells (x, y) every few minutes |
| 2 | Calculate speed, distance moved and direction relative to the chemoattractant source |
| 3 | Calculate f and then φ from the direction |
| 4 | Calculate RMS speed (v), calculate φ average *($\phi_a$) |
| 5 | Calculate X (flux, cm²/sec) = $\phi_a \cdot v/\nabla a$ |
| 6 | Calculate $J_{net}$ = (X · c · $\nabla$ a) · A · t (unit = cells) |

$\nabla$a = is the gradient in chemoattractant (units=M/cm); this is often approximated as the average concentration of attractant divided by the membrane thickness. $\nabla$a can also be more accurately calculated using diffusion equations.

c=concentration of cells in the chamber (units=cells/cm³).

A=the area of membrane through which the cells migrate (units=cm²).

t=time over which net flux, $J_{net}$ is measured.

B. Population Tracking

For population-based analyses, one measures the number of cells at one or more selected points in time ($t_1$, $t_2$, $t_3$, . . . $t_n$), or the total number of cells over a selected period of time, that pass through the interrogation zone after initial exposure of the cells sample to a concentration gradient of chemotactic agent, at $t_0$.

In one embodiment, individual cell positions in an interrogation zone are determined once, after a suitable period of time has lapsed (e.g., 30 minutes), subsequent to initial exposure to a chemotactic agent at $t_0$.

Typically, the number of cells in the interrogation zone will be zero at $t_0$. In another embodiment, several determinations are made successively (e.g., every 15 minutes) over a period of time (e.g., 2 hours). In a further embodiment, the total number of cells that pass through the interrogation zone are counted over a set period of time (e.g., 2 hours).

The computing means, e.g., an IBM®-compatible PENTIUM®-class personal computer, or similar products readily available from various manufacturers, then processes the electronic readable (digitized) data representing the positions of individual detected cells for a population-based analysis. In this regard, the computing device is programmed, by methods known in the art, to compare the distribution of detected, position-assigned cells in the interrogation region at two spaced time intervals. In one embodiment, the programmed computing device functions to compare the total number of detected cells whose positions are within the interrogation region at each of two spaced time intervals. In another embodiment, the programmed computing device functions to (i) calculate a motion vector in the direction of the concentration gradient for each of the detected cells in the interrogation region, over the spaced time interval, and (ii) determine an average motion vector from the calculate individual vectors of the detected cells in the interrogation region.

It should be appreciated that the present invention provides the ability to demonstrate distributions/histograms from data representing the positions of individual cells. By determining the distributions of cell positions within an interrogation zone on at least two temporally-spaced occasions, it is possible to ascertain aggregate movement in relation to the concentration gradient of chemotactic agent.

What is claimed is:

1. A method of determining the motile response to a chemotactic agent of a selected type of cell contained in a sample of mixed cell types, comprising the steps of:

(i) labeling said selected type of cell, contained in said mixed-cell sample, with a fluorescent compound preferentially binding to said selected type of cell;

(ii) establishing a concentration gradient of a chemotactic agent in an assay chamber;

(iii) adding said mixed cell sample into said assay chamber proximate to said concentration gradient;

(iv) optically scanning a region of said concentration gradient;

(v) electronically detecting areas of peak fluorescence representative of an individual cell of said selected type of cell in the sample;

(vi) identifying positions of said individual cells of said selected type of cell along the region;

(vii) repeating steps (iv) to (vi) to again identify individual cell location within said assay chamber at at least one additional time spaced interval; and (viii) analyzing the positions of individual cells of said selected type of cell to determine the motility of said selected type of cell.

2. The method of claim 1, wherein wavelengths of the excitation beam and excitation and emission wavelengths of the fluorescent compound are above the absorption and autofluorescence wavelengths of other fluorescent compounds in the sample.

3. The method of claim 1, wherein a plurality of different samples ere analyzed to determine the motility of said selected type of cell in a parallel fashion upon a single substrate.

4. The method of claim 3 further comprising:

selecting a plurality of cell types and labeling each of said plurality of selected cell types with a unique fluorophore; and assaying the motility of each of said plurality of selected cell types upon a single substrate in a parallel fashion.

* * * * *